Figure 1:
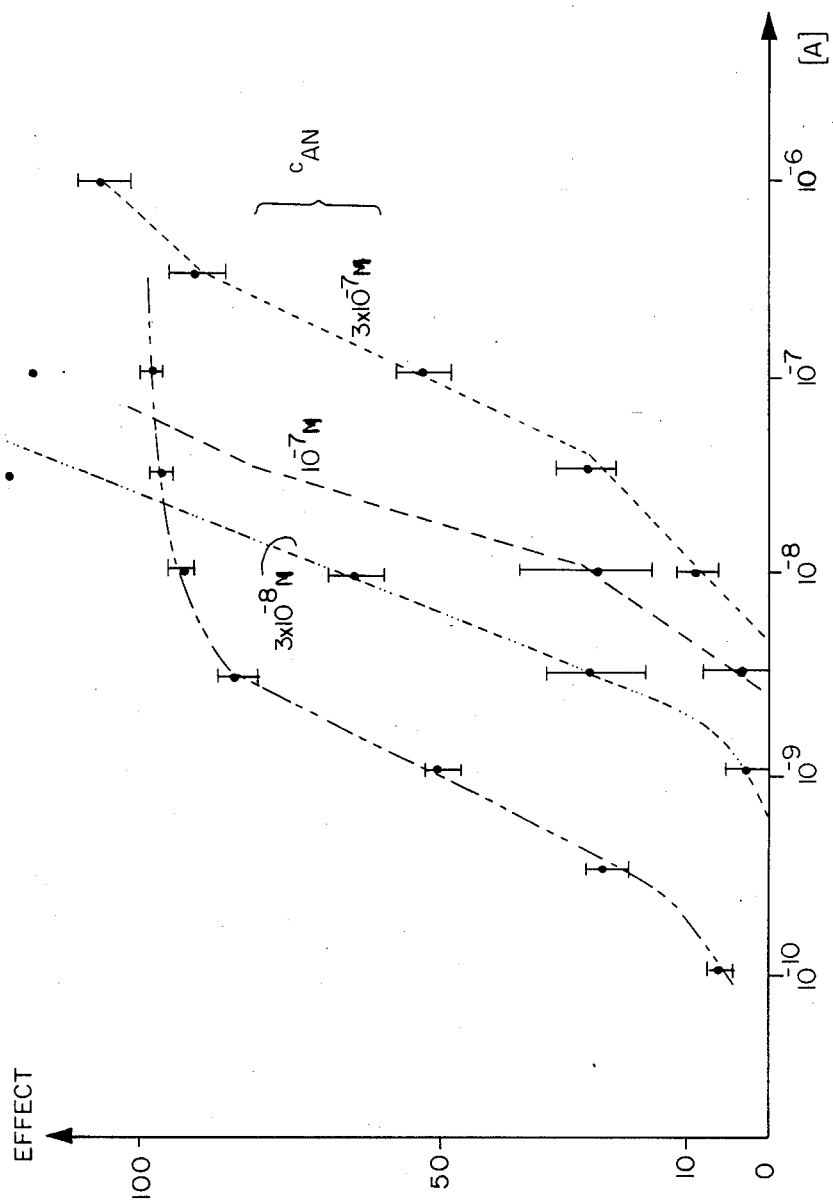

United States Patent [19]

Marchand et al.

[11] Patent Number: 4,703,057
[45] Date of Patent: Oct. 27, 1987

[54] BETA-BLOCKING THIOCHROMAN DERIVATIVES, COMPOSITIONS AND METHOD OF USE THEREFOR

[75] Inventors: Bernard Marchand, Checy; Yves M. Gargouil, Paris, both of France

[73] Assignee: ADIR Et Compagnie, Neuilly-sur-Seine, France

[21] Appl. No.: 913,351

[22] Filed: Sep. 30, 1986

[30] Foreign Application Priority Data

Oct. 4, 1985 [FR] France ................................. 85 14755

[51] Int. Cl.[4] ..................... A61K 27/00; C07D 65/00; C07D 335/06
[52] U.S. Cl. ...................................... 514/432; 549/23
[58] Field of Search ........................... 549/23; 514/432

[56] References Cited

FOREIGN PATENT DOCUMENTS 2092004 11/1975 France ................................... 549/23
1561153 2/1980 United Kingdom ................... 549/23

OTHER PUBLICATIONS

Verbeuren et al, CA vol. 103, 1985, 103: 206196x.

*Primary Examiner*—Henry R. Jiles
*Assistant Examiner*—J. G. Mullins
*Attorney, Agent, or Firm*—Gordon W. Hueschen

[57] ABSTRACT

The invention relates to 1-tert.-butylamino-3-(4-hydroxy-8-thiochromanyloxy)-2-propanol.

6 Claims, 3 Drawing Figures

BETA-BLOCKING THIOCHROMAN DERIVATIVES, COMPOSITIONS AND METHOD OF USE THEREFOR

The present invention relates to a new compound of thiochroman, a process for the preparation thereof, and pharmaceutical compositions containing it.

Some compounds of 1-alkylamino-3-(8-thiochromanyloxy)-propanol having interesting pharmacological properties are known, especially 1-tert.-butylamino-3-(8-thiochromanyloxy)-2-propanol which is described in French Pat. No. 71.11445 and in British Pat. No. 1.561.153. 1-tert.-butylamino-3-(8-thiochromanyloxy)-2-propanol or 8-(3-tert.-butylamino-2-hydroxypropoxy)-thiochroman or tertatolol belongs to the class of beta-blocking agents and has cardiovascular properties which are used especially in the treatment of arterial hypertension. The Applicant has now discovered a new beta-blocking agent derived from 1-tert.-butylamino-3-(8-thiochromanyloxy)-propanol which has a chemical structure that is very close to that of tertatolol and a beta$_1$-adrenolytic activity which is twice that of tertatolol.

The present invention relates more especially to a compound of thiochroman, 1-tert.-butylamino-3-(4-hydroxy-8-thiochromanyloxy)-2-propanol, which has the following chemical formula:

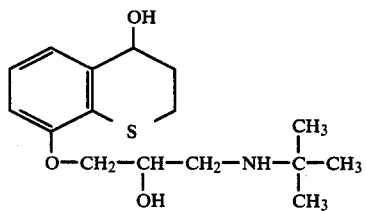

(I)

This compound contains two assymetric carbon atoms and therefore exists in racemic form and in the form of diastereoisomers which as such form part of the invention.

The invention also relates to the addition salts of the compound of the formula I, with a pharmaceutically acceptable mineral or organic acid. Of the acids used to form these salts there may be mentioned phosphoric acid, hydrochloric acid, sulphuric acid, acetic acid, propionic acid, citric acid, oxalic acid, benzoic acid, etc.

The present invention also relates to a process for the preparation of the compound of the general formula I, characterised in that 8-methoxy-4-thiochromanone of the formula II:

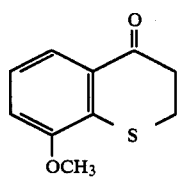

(II)

is reduced by means of a boron hydride to 8-methoxy-4-thiochromanol of the formula III:

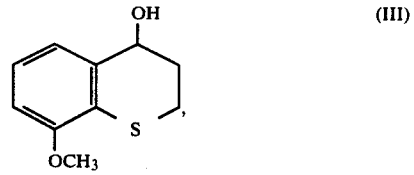

(III)

which is then demethylated, by means of a thiolate, to obtain 8-hydroxy-4-thiochromanol of the formula IV:

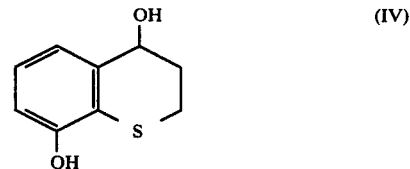

(IV)

with which there is reacted 1-chloro-2,3-epoxypropane to yield 3-(4-hydroxy-8-thiochromanyloxy)-1,2-epoxypropane of the formula V:

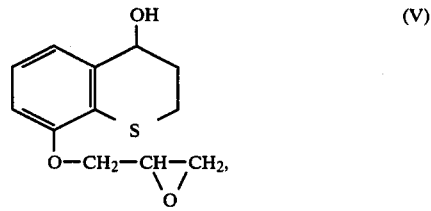

(V)

and this is condensed with tert.-butylamine to obtain the compound of the general formula I, and it is then possible to form its addition salts by the action of a pharmaceutically acceptable mineral or organic acid, or to separate it into its diastereoisomers which in turn may be converted into salts.

The 8-methoxy-4-thiochromanone can be prepared using the process described by F. Kollpfeiffer et al., (Ber. (1925), 58, 1654–1676). The reduction of thiochromanone to thiochromanol and the demethylation of the phenolic ether oxide are carried out by methods which are already known from the literature and are described in, respectively, Vogel's Textbook of Practical Organic Chemistry, Longman edition (1978), London, New York, 4th edition, p. 353–356 and Tetrahedron (1982), 38, 2721–2724 (L. Testaferri et al.). The reaction of 8-hydroxy-4-thiochromanol with 1-chloro-2,3-epoxypropane and the condensation of the product resulting from this reaction with a primary amine are described in French Pat. No. 2.092.004.

Because the compound of the formula I is very similar to tertatolol, its beta-blocking properties were foreseeable. On the other hand, it was not to be expected that this compound would have a beta$_1$-adrenolytic activity twice that of tertatolol. In fact, pharmacological tests in vitro have shown that 1-tert.-butylamino-3-(4-hydroxy-8-thiochromanyloxy)-2-propanol has a very high beta$_1$-adrenolytic activity.

The beta-blocking properties of the compound of the invention therefore enable it to be used in the treatment of hypertension, angina, myocardial ischaemia, disturbances of the cardiac rhythm, and cardiovascular manifestations of hyperthyroidism.

The invention also includes pharmaceutical compositions containing as active ingredient the compound of the formula I, a diastereoisomer thereof or an addition salt thereof with a pharmaceutically acceptable mineral or organic acid in association with a suitable inert, non-toxic excipient.

The pharmaceutical compositions thus obtained are advantageously presented in various forms, such as, for example, tablets, dragées, gelatine capsules, glossettes or other galenical preparations suitable for sublingual administration, suppositories, and solutions for injecting or drinking.

The pharmaceutical compositions according to the invention may also contain another active ingredient having a complementary or synergic action.

Of the latter active ingredients there may be mentioned a diuretic and, especially, a saluretic, or calcium antagonistic substance.

The dosage may vary widely depending on the age and weight of the patient, the nature and severity of the disorder and also the route of administration. The preferred route of administration is buccal or parenteral administration. In general, the unit dose will range from 0.1 to 5 mg and the daily dose which may be used therapeutically in humans will range from 0.1 to 5 mg.

The following Examples, given by way of nonlimiting examples, illustrate the invention. Melting points were determined using the Köfler block.

EXAMPLE 1

8-methoxy-4-thiochromanol.

89 mmol of 8-methoxy-4-thiochromanone are dissolved in 70 ml of a mixture of methanol and tetrahydrofuran (¾). 134 mmol of sodium borohydride dissolved in 50 ml of aqueous methanol (50%) are added. After stirring for 1 hour at room temperature and then extracting with methylene chloride, the resulting product is recrystallised from a mixture of methanol and diethyl ether (1/10).

Yield 87%.

Melting point of the resulting product 91°–93° C.

EXAMPLE 2

8-hydroxy-4-thiochromanol.

A solution of 25 mmol of the 8-methoxy-4-thiochromanol obtained previously in 50 ml of hexamethylphosphorotriamide (HMPT) is heated to 120° C. 2.5 equivalents of sodium isopropanethiolate are added with the application of heat and the whole is stirred for 1½ hours at 120° C. under nitrogen.

The cooled mixture is poured into 150 ml of N hydrochloric acid and extracted with methylene chloride. After washing the organic phase until the HMPT has disappeared and evaporating off the solvent, the mixture is recrystallised from a mixture of methylene chloride and diethyl ether (1/1). 4.2 g of 8-hydroxy-4-thiochromanol are obtained. Yield 85%.

EXAMPLE 3

1-tert.-butylamino-3-(4-hydroxy-8-thiochromanyloxy)-2-propanol.

48.2 g of 8-hydroxy-4-thiochromanol are dissolved in 150 ml of acetone. 104 ml of 1-chloro-2,3-epoxypropane are added, followed by 109 g of potassium carbonate. The whole is refluxed for 8 hours. It is filtered and evaporated at 50° C. under reduced pressure (12 mm Hg) until a constant weight is reached. 58 g of a mixture of epoxide and halohydrin are obtained. 48 g of this mixture are treated with 180 ml of tert.-butylamine in 100 ml of isopropanol.

The whole is refluxed for 7 hours. After evaporation of the amine and the solvent, the oily residue is taken up in methylene chloride and washed with N ammonium hydroxide.

After removal of the solvent at 40° C. under reduced pressure, 1-tert.-butylamino-3-(4-hydroxy-8-thiochromanyloxy)-2-propanol is obtained in the form of an oil.

Yield 50%.

The spectral characteristics of 1-tert.-butylamino-3-(4-hydroxy-8-thiochromanyloxy)-2-propanol in the form of a base are as follows:

A. Infra-red spectrum, obtained with the product dispersed in potassium bromide:

$\nu_S$ OH and NH between 3000 cm$^{-1}$ and 3700 cm$^{-1}$;
$\nu_S$ C=C 1570 cm$^{-1}$;
$\nu_S$ C—O—C 1260 cm$^{-1}$ and 1035 cm$^{-1}$.

B. Proton nuclear magnetic resonance spectrum, recorded at 200 MHz dissolved in deuterochloroform: 1.2 ppm s 9H; 2.0 ppm m 1H; 2.4 ppm m 1H; 3.0 ppm m 3H; 3.25 ppm m 1H; 4.0 ppm m 3H; 5.8 ppm m 1H; 6.75 ppm m 3H; 7 ppm m 3H (3H exchangeable with D$_2$O between 6.75 and 7 ppm).

C. Mass spectrum recorded at 80 eV, on electronic impact (m/z): 311 (M$^+$ 3.12%), 296 (6.06%), 267 (10.82%), 182 (10.39%), 164 (5.11%), 163 (6.41%), 114 (6.75%), 86 (100%).

The acetate of 1-tert.-butylamino-3-(4-hydroxy-8-thiochromanyloxy)-2-propanol is obtained after the addition of 12 ml of glacial acetic acid to a solution of the oil obtained previously in 1 liter of diethyl ether. After filtration of the resulting precipitate, washing, while warm, with acetonitrile and recrystallisation from a mixture of acetonitrile and methanol (10/1), 41 g of acetate are obtained.

Melting point 130°–135° C.

Elemental analysis of the acetate (C$_{18}$H$_{29}$NO$_5$S) Theory: C 58.19%; H 7.86; N 3.77; S 8.63. Found: C 58.18%; H 7.58; N 3.80; S 8.76.

PHARMACOLOGICAL STUDY

EXAMPLE 4

Evaluation of the beta$_1$-adrenolytic activity in vitro.

The beta-blocking properties of the compound of the formula I and, more precisely, the intensity of the beta$_1$-adrenolytic activity in vitro were evaluated on the basis of the inhibition of the chronotropic responses of the right auricle of rats, when stimulated by isoprenaline. The effects of this compound were compared with those of tertatolol and propanolol, the latter being a reference beta-blocking agent.

The studies are carried out on the right auricle which has been removed from male Wistar rats weighing from 300 to 400 g. After sacrifice, the heart is removed and the right auricle is quickly dissected and then placed in an isolated-organ bath containing a physiological solution which is kept at a temperature of 37° C. and is oxygenated by a mixture of 95% oxygen and 5% carbon dioxide. The auricle is connected to an electromechanical sensor. An initial force of 400 mg is applied. The cardiac frequency of the auricle is recorded via an amplifier/integrator. First, after a stabilisation period of 40 min., cumulative doses (3×10$^{-10}$M, 10$^{-9}$M, 3×10$^{-9}$M . . . ) of isoprenaline are added to the bath every 3 min. until the maximum chronotropic effect is reached, in order to establish a control curve for the agonist alone. Secondly, in order to establish the agonist/antagonist interaction curve, a concentration of the compound of the formula I, of tertatolol or of propanolol is added to the bath 10 min. before cumulative doses ($10^{-9}$M, $3 \times 10^{-9}$M ...) of isoprenaline are added. A single concentration of antagonist is tested per preparation.

FIG. 1 shows the dose/response curves for isoprenaline in the presence and in the absence of propanolol.

[A]=molar concentration of ISOPROTERENOL (logarithmic scale).

Effect=percentage effect relative to the maximum effect on the rhythm (b.p.m.).

$C_{AN}$=antagonist concentrations.

Figure 2:
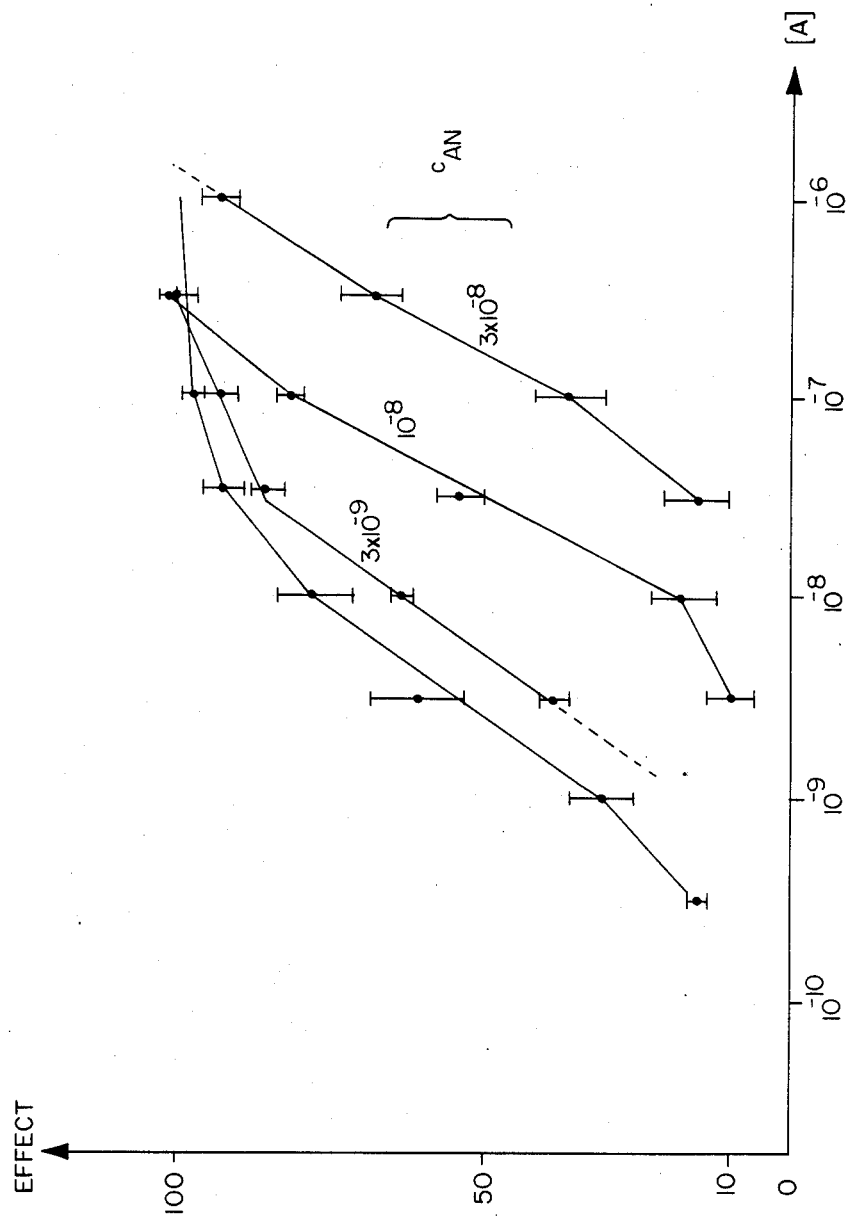

FIG. 2 shows the dose/response curves for isoprenaline in the presence and in the absence of tertatolol.

[A]=molar concentration of ISOPROTERENOL (logarithmic scale).

Effect=percentage effect relative to the maximum effect on the rhythm (b.p.m.).

$C_{AN}$=antagonist concentrations.

Figure 3:
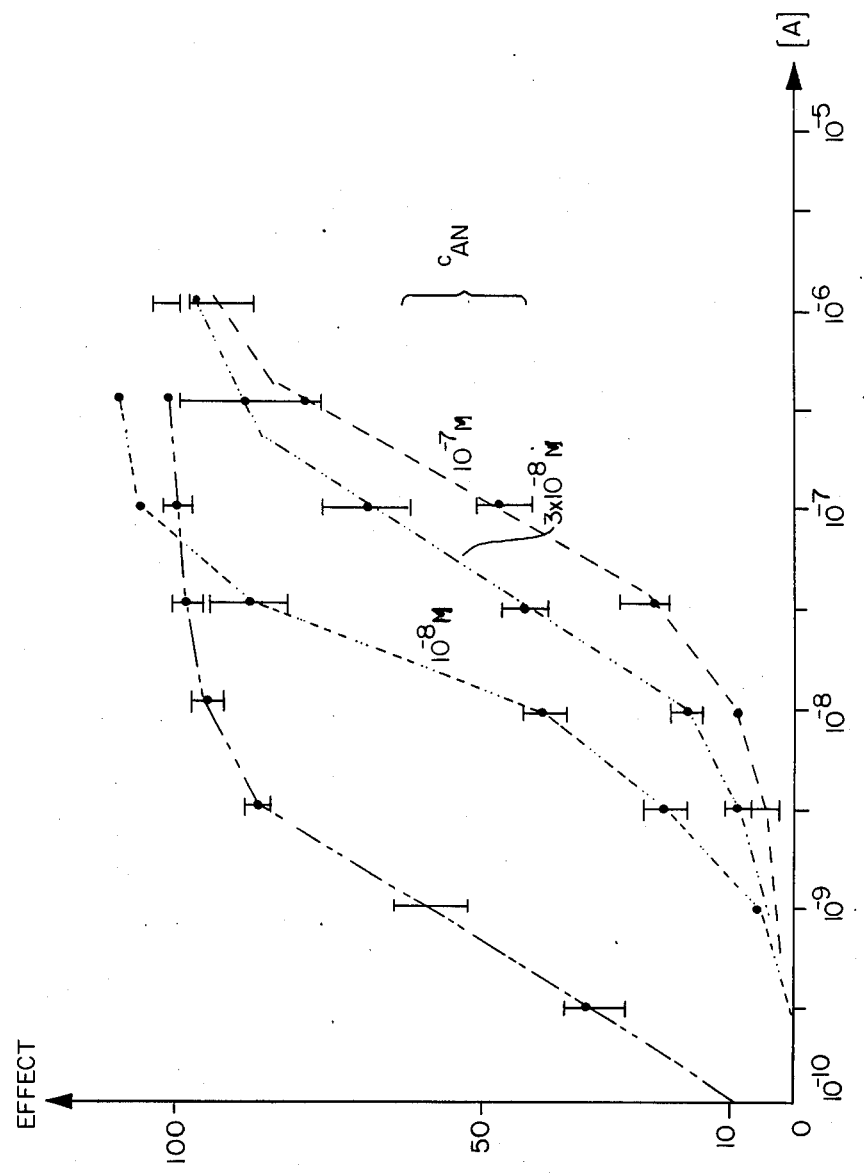

FIG. 3 shows the dose/response curves for isoprenaline in the presence and in the absence of the compound of the formula I.

[A]=molar concentration of ISOPROTERENOL (logarithmic scale).

Effect=percentage effect relative to the maximum effect on the rhythm (b.p.m.).

$C_{AN}$=antagonist concentrations.

The $pA_2$ value, which allows a competitive antagonism to be evaluated quantitatively (Guidicelli J. F., J. Pharmacol. (Paris) 1971, 2(3), 373), is calculated for the three products. The $pA_2$ value represents the cologarithm of the molar concentration of the antagonist which requires the concentration of agonist to be doubled in order that a response of the same intensity as that recorded with the agonist alone is again obtained.

For each experiment, the $pA_2$ value is calculated according to the method of Van Rossum (Arch. Int. Pharmacodyn (1963) 143, 299) using the equation $$pA_2 = pAx + \log(x-1).$$

pAx represents the cologarithm of the molar concentration of the antagonist.

x represents the displacement of the curve in mm (value of log (x−1) given by Van Rossum's table).

Student tests (paired series) are carried out in order to permit the averaging of the control curves and of the test curves.

Tables 1, 2 and 3 summarise the $pA_2$ values calculated for propanolol, tertatolol and the compound of the formula I, respectively, in the various tests.

TABLE 1

| Antagonist concentration (M) | pAx | x | log (x − 1) | pA₂ |
| --- | --- | --- | --- | --- |
| $3 \times 10^{-8}$ | 7.52 | 30.5 | 0.97 | 8.49 |
| $3 \times 10^{-8}$ | 7.52 | 28.5 | 0.9 | 8.42 |
| $3 \times 10^{-8}$ | 7.52 | 28.5 | 0.9 | 8.42 |
| $10^{-7}$ | 7 | 36 | 1.7 | 8.17 |
| $10^{-7}$ | 7 | 26.5 | 0.82 | 7.82 |
| $10^{-7}$ | 7 | 25.5 | 0.78 | 7.78 |
| $10^{-7}$ | 7 | 33.5 | 1.98 | 8.08 |
| $3 \times 10^{-7}$ | 6.52 | 56.0 | 1.86 | 8.38 |
| $3 \times 10^{-7}$ | 6.52 | 68.0 | 2.26 | 8.78 |
| $3 \times 10^{-7}$ | 6.52 | 55.0 | 1.83 | 8.35 |
| $3 \times 10^{-7}$ | 6.52 | 57.0 | 1.89 | 8.41 |
| Propanolol $\overline{pA_2} = 8.28 \pm 0.089$ | | | | |
| (n = 11) | | | | |

TABLE 2

| Antagonist concentration (M) | pAx | x | log(x − 1) | pA₂ |
| --- | --- | --- | --- | --- |
| $10^{-9}$ | 9 | 6 | −0.23 | 7.77 |
| $10^{-9}$ | 9 | 7 | −0.15 | 8.85 |
| $10^{-9}$ | 9 | 3.5 | −0.51 | 8.49 |
| $3 \times 10^{-9}$ | 8.52 | 25.5 | 0.78 | 9.3 |
| $3 \times 10^{-9}$ | 8.52 | 27 | 0.84 | 9.36 |
| $3 \times 10^{-9}$ | 8.52 | 19.5 | 0.54 | 9.06 |
| $10^{-8}$ | 8 | 41 | 1.35 | 9.35 |
| $10^{-8}$ | 8 | 46 | 1.52 | 9.52 |
| $10^{-8}$ | 8 | 47 | 1.55 | 9.55 |
| $3 \times 10^{-8}$ | 7.52 | 35 | 1.13 | 8.65 |
| $3 \times 10^{-8}$ | 7.52 | 32.5 | 1.05 | 8.57 |
| Tertatolol $\overline{pA_2} = 9.04 \pm 0.118$ | | | | |
| (n = 11) | | | | |

TABLE 3

| Antagonist concentration (M) | pAx | x | log(x − 1) | pA₂ |
| --- | --- | --- | --- | --- |
| $10^{-8}$ | 8 | 37.5 | 1.22 | 9.22 |
| $10^{-8}$ | 8 | 38 | 1.24 | 9.24 |
| $10^{-8}$ | 8 | 31 | 0.99 | 8.99 |
| $3 \times 10^{-8}$ | 7.52 | 55.5 | 1.84 | 9.36 |
| $3 \times 10^{-8}$ | 7.52 | 57 | 1.89 | 9.41 |
| $3 \times 10^{-8}$ | 7.52 | 50 | 1.66 | 9.18 |
| $3 \times 10^{-8}$ | 7.52 | 73 | 2.43 | 9.95 |
| $10^{-7}$ | 7 | 56 | 1.86 | 8.86 |
| $10^{-7}$ | 7 | 63 | 2.10 | 9.10 |
| $10^{-7}$ | 7 | 69.5 | 2.31 | 9.31 |
| $10^{-7}$ | 7 | 61 | 2.03 | 9.03 |
| Compound of the formula I $\overline{pA_2} = 9.24 \pm 0.087$ | | | | |
| (n = 11) | | | | |

The experimental model used enabled the $pA_2$ values of propanolol, of tertatolol and of the compound of the formula I to be calculated. This measurement, in vitro, of the "potency" of the antagonists is an indication of their inherent potential.

Propanolol served as a reference molecule. The $\overline{pA_2}$ value obtained is 8.28±0.089, a value which is close to that given in the literature. The curves obtained with tertatolol and the compound of the formula I (simple displacement to the right) allow it to be stated that isoprenaline-tertatolol antagonism or isoprenaline-compound of the formula I antagonism is of the competitive type and therefore that only one type of receptor is involved in this mechanism.

For tertatolol, the corresponding $\overline{pA_2}$ value is 9.04±0.118. This compound has a very different structure from that of propanolol and therefore proves to be 6 times more powerful than the latter beta-blocking agent. On the other hand, the beta$_1$-antagonistic activity of the compound of the formula I, which is very close to tertatolol, is very surprisingly twice that of tertatolol. The $\overline{pA_2}$ value obtained is 9.24±0.087.

PHARMACEUTICAL PREPARATION

EXAMPLE 5

Gelatine capsules containing 0.005 g of 1-tert.-butylamino-3-(4-hydroxy-8-thiochromanyloxy)-2-propanol

| | |
|---|---|
| 1-tert.-butylamino-3-(4-hydroxy-8-thiochromanyloxy)-2-propanol | 0.0050 g |
| Corn starch | 0.0320 g |
| Microcrystalline cellulose | 0.0262 g |
| Lactose | 0.0720 g |
| Colloidal silica | 0.0003 g |
| Magnesium stearate | 0.0015 g |
| Talc | 0.0030 g | for a white gelatine capsule, size no. 3.

We claim:

1. Compound of the formula I:

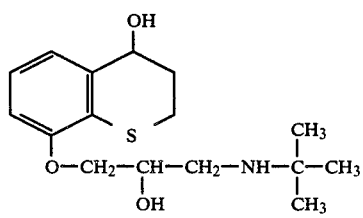

in racemic form or in the form of an optical isomer or an addition salt thereof with a pharmaceutically-acceptable mineral or organic acid.

2. Pharmaceutical composition having beta-blocking activity containing as active ingredient an effective beta-blocking amount of compound according to claim 1, in association or in admixture with a pharmaceutically acceptable, inert, non-toxic excipient or carrier.

3. Pharmaceutical composition according to claim 2, containing the active ingredient in an amount of from 0.1 to 5 mg.

4. Method of treating a patient in need of treatment with a beta-blocker which comprises the step of administering an effective beta-blocking amount of a compound of claim 1 to said patient.

5. Method of treating a patient in need of treatment with a beta-blocker which comprises the step of administering an effective beta-blocking amount of a composition of claim 2 to said patient.

6. Method of treating a patient in need of treatment with a beta-blocker which comprises the step of administering an effective beta-blocking amount of a composition of claim 3 to said patient.

* * * * *